United States Patent [19]

Ogden et al.

[11] Patent Number: 5,646,357
[45] Date of Patent: Jul. 8, 1997

[54] AIR SAMPLING SYSTEM AND FLOW CALIBRATION SYSTEM FOR SAME

[75] Inventors: Michael Wayne Ogden; David Lynn Heavner, both of Winston-Salem, N.C.

[73] Assignee: R. J. Reynolds Tobacco Company, Winston-Salem, N.C.

[21] Appl. No.: 641,788

[22] Filed: May 2, 1996

Related U.S. Application Data

[63] Continuation of Ser. No. 249,487, May 26, 1994, Pat. No. 5,551,311.

[51] Int. Cl.$^6$ .................................................. G01N 1/16
[52] U.S. Cl. .................... 73/863.31; 73/863.23; 73/28.01; 73/31.02; 436/106; 422/61; 422/88; 422/119
[58] Field of Search ................ 73/28.01, 31.01, 73/31.02, 863.12, 963.21, 963.23, 963.31; 422/61, 83, 88, 119; 436/106, 175, 177, 178, 181

[56] References Cited

U.S. PATENT DOCUMENTS

| | | |
|---|---|---|
| 2,353,828 | 7/1944 | Hyde . |
| 3,507,147 | 4/1970 | Llewellyn . |
| 3,765,247 | 10/1973 | Riggs . |
| 3,871,827 | 3/1975 | Seiler et al. . |
| 3,881,359 | 5/1975 | Culbertson . |
| 3,903,745 | 9/1975 | Bolser . |
| 4,324,146 | 4/1982 | Born . |
| 4,461,184 | 7/1984 | Gandhi et al. . |
| 4,569,235 | 2/1986 | Conkle et al. . |
| 4,786,472 | 11/1988 | McConnell et al. . |
| 5,223,439 | 6/1993 | Rolle . |

FOREIGN PATENT DOCUMENTS

| | | |
|---|---|---|
| 58-154638 | 9/1983 | Japan . |
| 63-154936 | 6/1988 | Japan . |
| 522448 | 9/1976 | U.S.S.R. . |
| 1370502 | 1/1988 | U.S.S.R. . |

OTHER PUBLICATIONS

William C. Hinds, Sc.D. et al., *Concentrations of Nicotine and Tobacco Smoke in Public Places*, The New England Journal of Medicine, Apr. 17, 1975, vol. 292, pp. 844–845.
F.J. Lourence et al., *Flexible Bags Collect Gas Samples*, Control Engineering, Sep. 1967, p. 105.

*Primary Examiner*—Hezron E. Williams
*Assistant Examiner*—Daniel S. Larkin

[57] ABSTRACT

In air sampling system and a calibration system therefor are disclosed for use therewith in order to provide air sampling for, for example, environmental tobacco smoke aerosol in a portable personal air sampling system. The air sampling system utilizes a sampler head having a manifold block which allows for the collection of air for studying both the particulate and vapor phases of environmental tobacco smoke aerosol using only a single pump. An air flow calibrating system is utilized to measure and calibrate the air flowing through the two collection devices used in connection with the manifold block in which the air flow through the two sampling assemblies is simultaneously read out.

20 Claims, 3 Drawing Sheets

AIR SAMPLING SYSTEM AND FLOW CALIBRATION SYSTEM FOR SAME

This is a continuation of application Ser. No. 08/249,487 filed on May 26, 1994, now U.S. Pat. No. 5,551,311.

FIELD OF THE INVENTION

The present invention relates generally to atmospheric or air sampling systems. More particularely, the present invention relates to portable air sampling systems for personal and area use and apparatus for calibrating such systems.

BACKGROUND OF THE INVENTION

Atmospheric air, either indoors or outdoors, contains gaseous material and particulate matter. For example, air which is inhaled by human beings typically includes gases such as nitrogen, oxygen and carbon dioxide; water vapor, and particulate material which has dust, spores and the like.

A great deal of interest has developed in studying the nature, characteristics and quality of environmental air. In particular, there is great interest on the part of the Occupational Safety and Health Administration (OSHA) in studying indoor air quality. The quality of air in indoor settings, such as "white collar" office environments, is typically the subject of adverse claims by workers. There is also a good deal of interest in the study of indoor settings in homes as well as in other enclosed areas. The study of the indoor air quality in such settings can provide valuable information with regard to providing the effective ventilation and/or air circulation or recirculation within those enclosed areas. Such studies can also allow for the analysis of any contaminants found within those indoor environments so that steps may be taken to minimize such undesirable materials in order to improve the air quality.

Generally speaking, then, it is desirable to study environmental air in industrial areas such as factories, chemical plants and warehouses; in agricultural areas such as barns and silos; in social areas such as hotels, restaurants, bars, auditoriums and stores; and in personal areas such as homes and apartments and during travel. In particular, it is desirable to sample and analyze environmental air in such indoor spaces for asbestos fibers, dust, volatile organic compounds, pollen, coal dust, gasoline or diesel engine exhaust, smoke, wood stove exhaust or metal ions or material such as lead, beryllium, uranium, cadmium, zinc or selenium.

It is desirable to collect and analyze environmental atmospheric samples in a particular setting or settings over a fairly long period of time, such as a 24 hour period. However, for a realistic and representative assessment of the environmental air being sampled, it is useful to sample the particulate and vapor phases of the, for example, environmental tobacco smoke (ETS) aerosol, or other environmental material. Furthermore, it is desirable to utilize equipment which users can move along with them in different environments which the users may encounter during, for example, an 18–24 hour period. In order to be useful then, the sampling and collection system for environmental air samples should involve quiet, small and portable equipment such that it does not disturb the user while at the same time it dutifully monitors the user's environment. An air sampling system, such as the one disclosed herein, meets such requirements and provides a realistic and representative assessment of the particular indoor settings in which it is used because it is relatively unobtrusive and does not greatly affect human behavior during the sample collection periods.

It is, therefore, desirable to provide a portable, air sampling system which is capable of simultaneously monitoring both the particulate and vapor phases of, for example, ETS aerosol and which is capable of being easily moved by the user to other environments and used over a continuous period of time during which the sampling occurs. It is also desirable to utilize a simple yet effective system for calibrating such an air sampling system in order to ensure the accuracy of the sample collected by the air sampling system.

One approach to providing a portable air sampling device is disclosed in U.S. Pat. No. 4,786,472, which discloses a portable air sampling device in the shape of a briefcase. The components contained within the briefcase are capable of sampling air for analysis. For example, air is introduced into the briefcase through inlet ports and that air can be monitored for components of environmental tobacco smoke. Separate inlet ports are utilized to provide inlet air to a chemical collection device such as a sorbent tube for collecting nicotine and a filter for collecting respirable suspended particulate matter. In addition, a chemical detector for monitoring carbon monoxide levels and provisions for monitoring the environmental temperature and barometric pressure are also provided. Data is stored on a microcomputer within take briefcase for later transfer to a computer for data analysis.

Unlike the present invention, the device set forth in U.S. Pat. No. 4,786,472 requires the use of two pumps one for each separate particulate and vapor phase collection and sampling system. The present invention, on the other hand, utilizes a single pump and collects both the particulate and vapor phases of the environmental tobacco smoke aerosol through a single manifold. Thus, the air sampling system of the present invention is very small and is therefore more easily transported by the user from place to place within his personal environment. In addition, the present system will run for longer time periods than that discussed in U.S. Pat. No. 4,786,472. A novel system for calibrating the air sampling system of the present invention is also provided.

Another approach to a portable air sampler is disclosed in U.S. Pat. No. 4,569,235, which discloses a sequential air sampler assembled within a portable industrial housing which allows the air sampler to operate by either battery or line power. The system disclosed in U.S. Pat. No. 4,569,235 utilizes a plurality of components through which air samples are sequentially drawn utilizing a single pump and a flow rate control system. However, the system disclosed in U.S. Pat. No. 4,569,235, by utilizing a single vacuum pump, does not simultaneously sample environmental air for particulate and vapor phases of environmental tobacco smoke aerosol, nor is that system "portable", in other than the industrial sense of that word.

Yet another approach to an air sampling device which is used for sampling tobacco smoke in public places is disclosed in the Apr. 17, 1975 issue of the New England Journal of Medicine, Vol. 292, pages 844–845, in an article entitled "Concentrations of Nicotine and Tobacco Smoke in Public places", by Hinds et al. That article discloses, in FIG. 1, a sampling system which utilizes a pump which is used to draw air through a filter and is directed to the measurement of only the particulate phase of tobacco smoke. While disclosing a portable air sampling system, the sampling system of Hinds et al. is not capable of simultaneously collecting particulate and vapor phase samples of environmental tobacco smoke aerosol.

SUMMARY OF THE INVENTION

In view of the foregoing, it should be apparent that there still exists a need in the art for a portable air sampling system which is capable of simultaneously collecting air samples for particulate and vapor phases of environmental tobacco smoke aerosol in a simple and precise manner in order to accurately sample the personal or other environment inhabited by a human user. It is, therefore, a primary object of this invention to provide an air sampling system for a user for sampling the particulate and vapor phases of environmental tobacco smoke aerosol in such a manner that only a single pump is necessary and which has particular application for use as a personal area environment testing system.

More particularly, it is an object of this invention to provide an air sampling system as aforementioned having simple and reliable components which operate in an unobtrusive manner and are not costly.

Still more particularly, it is an object of this invention to provide an air sampling system which can be readily and accurately calibrated using a calibration system in a simple and effective manner.

A further object of the present invention is to provide an air sampling system which utilizes easy to assemble components and which is easy for the user to operate.

Briefly described, these and other objects of the invention are accomplished by providing a sampler head having a manifold that enables the use of two sampling components in parallel; a filter cassette assembly and a sorbent tube. The use of two such sampling components in parallel allows the collection of both a filter and sorbent tube sample oh the same manifold using a single pump. The total air sample flow through the manifold is set on the air pump while a portion of the flow between the two collection devices is controlled by an orifice in the manifold assembly. The manifold assembly is designed to utilize two readily available and commonly used sample collection devices which allow for the simultaneous collection of samples of both the particulate and vapor phases of environmental tobacco smoke aerosol.

A flow measuring system is also disclosed which includes mass flow meters for direct simultaneous flow readings from both the sorbent tube and filter assembly. It also provides for measuring and calibrating the air flow through the filter cassette with the cyclone assembly in place. This feature is advantageous since use of the cyclone assembly changes the air flow rate through the filter assembly. Thus, the use of such a filter flow rate measuring system readily allows an accurate flow measurement through the filter cassette.

A data logging system is also provided which includes a personal computer-based software package and a bar code scanning system that enables the direct entry of system information on a sample-by-sample basis with a fast throughput time and minimal opportunity for error. The system creates records of outgoing sampling materials and stores them in a database along with relevant sampling information, such as pump flow rates, pump and battery identification numbers, etc. The record is then automatically retrieved to enable appending the additional information for incoming sampling materials.

With the foregoing and other objects, advantages and features of the invention that will become hereinafter apparent, the nature of the invention may be more clearly understood by reference to the following detailed description of the invention, the appended claims and to the several views illustrated in the drawings.

DETAILED DESCRIPTION OF THE INVENTION

Figure 1:
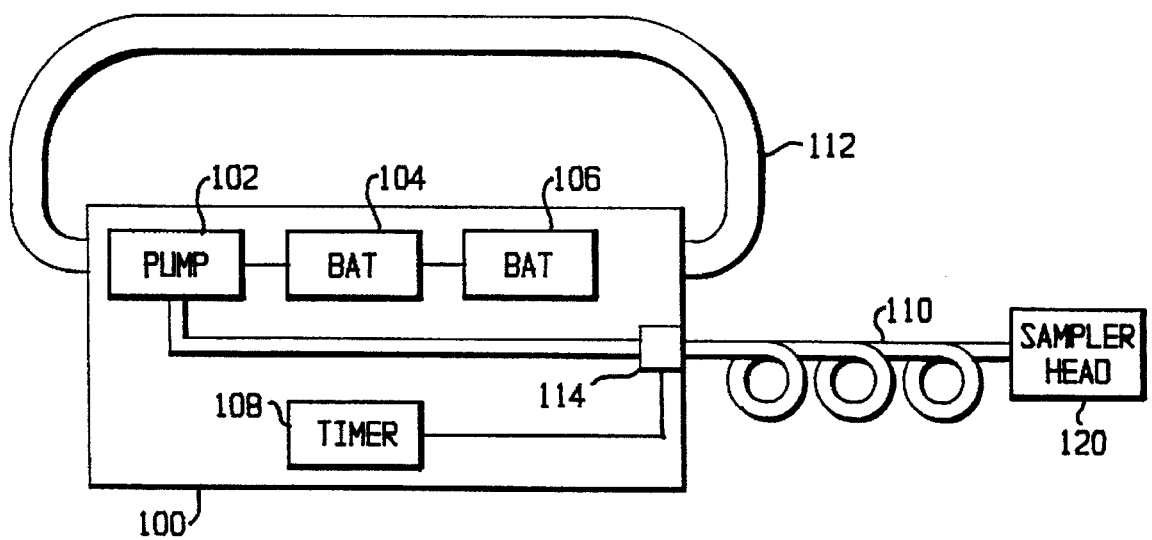
FIG. 1 is schematic diagram of the air sampling system of the present invention.

Referring now to the drawings in which like elements are designated by like reference numbers throughout, there is shown in FIG. 1 a schematic diagram of the air sampling system of the present invention which utilizes a box 100, such as an Underwater Kinetics Dry Box Model 409, available from Underwater Kinetics of San Marcos, Calif. The box enclosure 100 utilizes a foam material which is custom-plucked to enclose the components of the air sampling system which are contained in the box 100. The box enclosure 100 is provided with a shoulder strap 112 for suspending the box 100 from the body of a user, in the case of personal and environmental monitoring. Such methodology using the air sampling system of the present invention is currently required by OSHA. For general environmental air monitoring, it is not necessary to utilize the shoulder strap 112, or the strap may be used to locate the sampler over a chair back or on a door knob.

The custom-plucked material utilized in the box enclosure 100 is custom-plucked to enclose a pump 102, one or more batteries 104, 106, a timer assembly 108, a series pressure switch 114 and various tubing and electrical wiring. The box enclosure 100 serves two purposes- The first is to contain all of the materials, wiring, tubing and components discussed above. The second purpose of the enclosure 100 is to reduce the noise of the pump 102. The box enclosure 100 is provided with special latches and seals (not shown) for underwater use which results in a substantial soundproofing of the pump 102.

The pump 102 may preferably be a Model No. 224-50 "Special" pump available from SKC, Inc. of Eighty Four, Pa. Such a pump utilizes a plastic exhaust fitting in the pump case to muffle the noise generated by the pump in order to reduce the sound level of the pump during its operation. Thus, the new sampling system of the present invention may be utilized in, for example, a "white collar" office environment as well as in a user's home without generating any substantial noise which may disturb the user.

One or more batteries 104, 106, are electrically connected to the pump 102 in order to provide enough energy to continuously operate the pump 102 for at least 18 hours. If a shorter sampling time is desired, only a single one of the batteries 104, 106 could be utilized, which should operate a single battery pump, such as an SKC Model 224-50, for approximately 10–12 hours. The preferred battery configuration utilized for the pump 102 can be accomplished utilizing the battery jumper cable for the Model 224-50 pump, SKC Model No. 224-30-03 "Special".

A timer assembly 108, which may preferably be a 7-digit LCD elapsed timer, Model No. B121.01A, available from IVO Industries, inc. of Eatontown, N.J. is utilized together with a series pressure switch 114 to record the time in operation of the pump 102, and therefore of the air sampling system of the present invention. The series pressure switch, which may be a Model No. PSF 101, is available from World Magnetics Co. of Traverse City, Mich. The series pressure switch 114 is placed between the pump 102 and the exit of the tubing 110 which connects the sampler head 120 through the box enclosure 100 and to the pump 102.

A length of coiled tubing 110 is used to connect the sampler head 120 to the series pressure switch 114 and allows the user to place the sampler head 120 in a convenient sampling location without fear of catching the tubing 110 on an obstruction.

Figure 2:
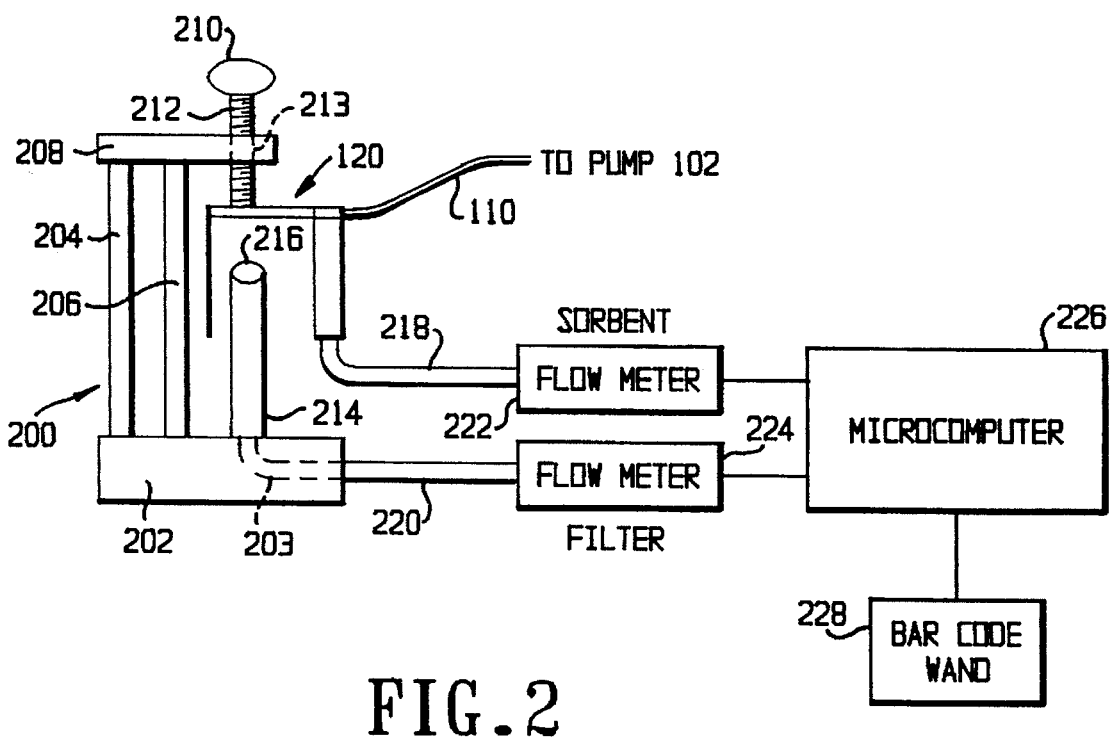
FIG. 2 is a combined perspective and schematic view of the calibration and data collection system used in collaboration with the air sampling system of FIG. 1.

Referring now to FIG. 2, there is shown a combination perspective and schematic diagram of the flow measuring system utilized to calibrate the air sampling system of the present invention. The air calibration system of FIG. 2 utilizes a fixture 200 which uses a base 202 to which two vertical supports 204 and 206 are fixedly attached perpendicular to the base 202.

The top portion 208 is removably secured to the ends of the vertical supports 204, 206 in such a manner that the top portion 208 is substantially parallel to the base portion 202.

The top portion 208 includes a knob 210 which is connected to a threaded shaft 212 which is threaded through and secured in a hole 213 in the top portion 208 of the fixture 200. A hollow tube 214 is secured at one end within the base 202 of the fixture 200. The opposite end of the hollow tube 214 utilizes an o-ring 216 which presses against the sampler head 120 which will be described hereinafter.

In order to calibrate the sampler head 120 of the present invention, the air flow through the sampler head 120 is tested both before the user utilizes the air sampling system of the present invention as well as after user has operated the air flow system of the present invention for a predetermined period of time. In order to utilize the air flow calibrating system of the present invention, the sampler head 120, is placed between the end of the threaded rod portion 212 of the knob 210 and the o-ring 216 of the hollow tube 214. The knob 210 is then rotated until the bottom of the filter cassette 304 fits snugly against the o-ring 216. A piece of tubing 218 is then connected between the outlet of the sorbent tube 302 and a sorbent flow meter 222. The sorbent flow meter 222 may preferably be a flow meter available from Sierra Instruments, Monterrey, Calif. as Model No. 821-1-(Air 1 SLM)-PS. A second piece of tubing 220 is connected at one end to the base 202. The base 202 has a drilled out passageway 203 which connects to the hollow tube 214. The second piece of tubing 220 is connected at its other end to a second flow meter 224 which provides flow information for the filter. The flow meter 224 may preferably be a Model No. 821-1-(Air 5 SLM)-PS, also available from Sierra Instruments The data output from the flow meters 222, 224 may be connected to a serial port of a microcomputer 226. The microcomputer 226 may preferably be an IBM or compatible personal computer having a microprocessor of the X86 family. For example, the microcomputer 226 may be a portable computer which utilizes a microprocessor of the 386 family or higher configuration with 4 megabytes of RAM memory and an appropriate size hard disk drive. Numerous such portable computers are commercially available and it is believed that no further discussion is necessary to enable one of ordinary skill in the art to select a suitable personal computer for use with the flow calibrating system of the present invention.

In order to easily provide for the input of data concerning the air sampling system components into the microcomputer 226, a bar code wand 228 may also be connected to the microcomputer 226. The bar code wand 228 can be utilized, in combination with unique bar codes on the pump 102, batteries 104, 106, filter cassette 304 and sorbent tube 302, as well as other components, to input information concerning those components into the microcomputer 226, as will be described further in connection with FIG. 4.

Figure 3:
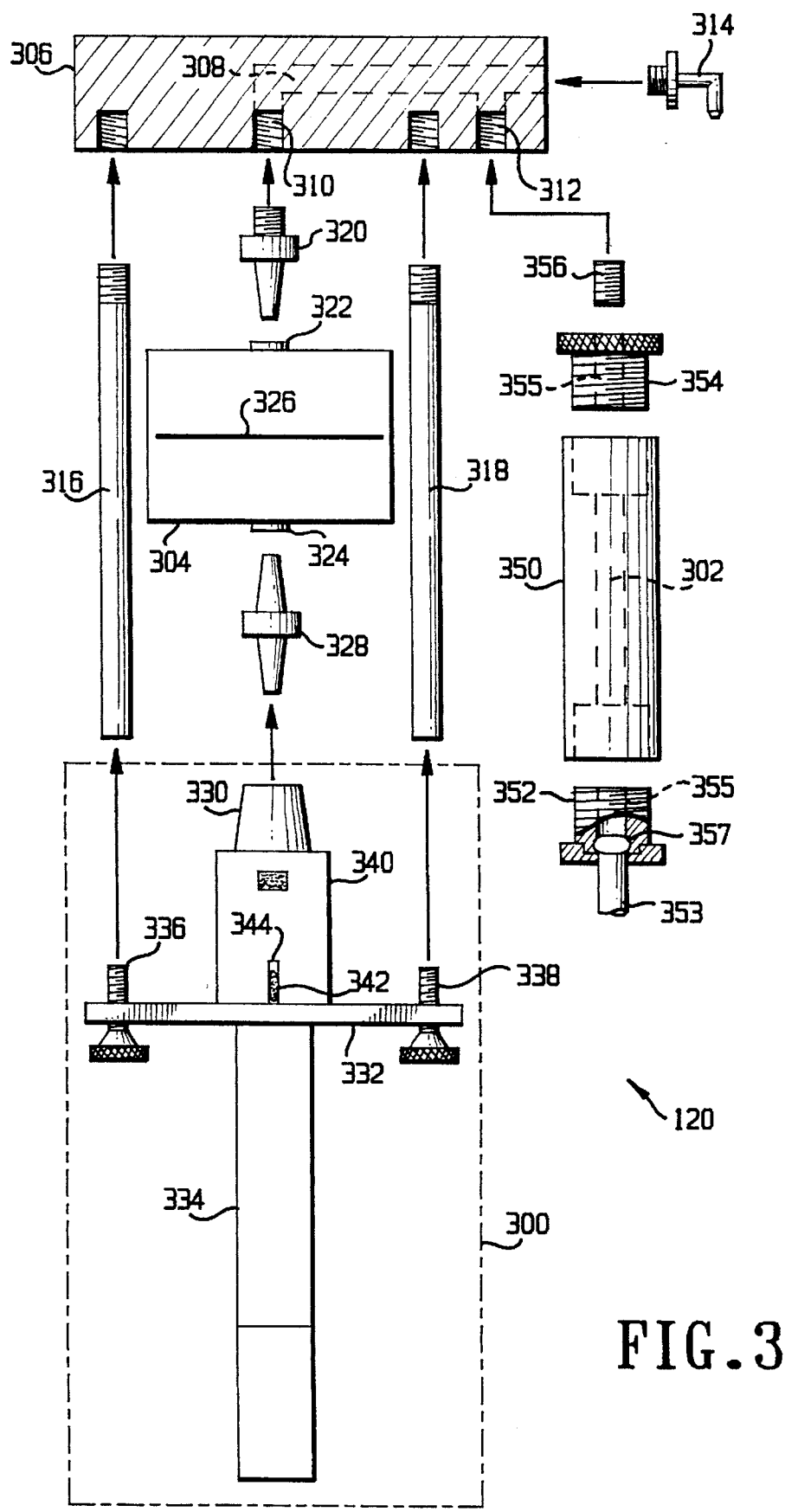
FIG. 3 is a pictorial diagram of the components which form the sampler head used with the air sampling system of the present invention; and 5

Referring now to FIG. 3, there is shown a pictorial diagram of components which form the sampler head 120. The sampler head 120 includes a manifold block 306 which may preferably be made from aluminum, or which can alternatively be made from PLEXIGLASS thermoplastic material or any other suitable material. The manifold block 306 contains a main air passageway 308 to which a fitting 314 is connected. The tubing 110 which is connected to the pump 102 is connected to the sampler head 120 by means of the fitting 314. The fitting 314 may preferably consist of a swivel connector with barbed hose fitting.

The main air passageway 308 is connected by means of two additional passageways 310 and 312 to the filter cassette 304 and to the sorbent tube 302. Because the filter passageway 310 and the sorbent passageway 312 are constructed in parallel, both of the sampling components, namely, the filter cassette assembly 304 and the sorbent tube 302, are connected in parallel to the pump 102, by means of the fitting 314 and the tubing 110. That allows the air sampling system of the present invention to collect both the filter and sorbent tube samples using a single manifold 306 and a single pump 102. An orifice 320 in the manifold assembly 306 is utilized to apportion the air flow created by the pump 102 between the filter cassette 304 and the sorbent tube 302. It acts in concert with an orifice 356 which connects the sorbent tube 302 to the manifold assembly 306. Alternatively, either or both of the orifices 320 and 356 can be replaced with adjustable needle valves which control the air flows. The total air flow through the manifold assembly 306 is preferably 2.2 liters per minute (1.7 LPM through the filter assembly 304 and 0.5 LPM through the sorbent tube 302) and is set by adjusting the air pump 102. The air sampling system of the present invention is therefore able to simultaneously collect the air samples containing particulate and vapor phases of environmental tobacco smoke aerosol.

The filter cassette 304 may preferably be a plastic filter cassette which is commercially available as Model No. M0003700 from Millipore Corporation of Bedford, Mass. It is designed to secure a circular 37 mm diameter FLUOROPORE film membrane filter which is a polytetrafluoroethylene film having a pore size of 1 micrometer. Such a filter is available from Millipore Corporation as Model No. FALP03700.

The outlet port 322 of the filter cassette assembly 304 is placed over a conically-shaped portion of an orifice fitting 320. The orifice fitting 320 is threaded into the filter air passageway 310 and sealed with an o-ring (not shown). Two aluminum tubes 316, 318 are also threaded into the manifold block 306. As discussed above, the filter 326 is contained within the filter cassette assembly 104 in a known manner.

A second conically-shaped orifice member 328, having two male luers at either end, is utilized to provide an air flow between the cyclone assembly 300 which is used to secure the cassette assembly 304 to the manifold 306 and the inlet port 324 of the filter cassette assembly 304. One luer of the orifice member 328 is placed into the input port 324 of the cassette filter assembly 304 and then the other luer of the orifice member 328 is secured into an outlet port 330 of the cyclone assembly 300. The cyclone assembly 300, which functions to separate particles of respirable size from the total particulate matter which would otherwise enter the filter cassette assembly 304, is available from Sensidyne Inc. of Clearwater, Fla. as part No. 2418584-0001. It is used to capture particles of size approximately greater than or equal to 3.5 micrometers, thus allowing respirable particles smaller than a known size to be passed to the filter 326.

The cyclone assembly 300 is carried by a plate 332 which has two thumb screws 336, 338 which are designed to screw into the opposite ends of the aluminum tubes 316, 318 which are not secured to the manifold block 306. The cyclone assembly 300 also includes a cyclone cylinder 334 and a top portion 340, of which the outlet 330 forms a part. The top portion 340 of the cyclone assembly 300 includes a notch 344 which contacts a pin 342 which is formed as a perpendicular element of the mounting plate 332 such that the cylinder 334 is rotatably secured to the plate 332. Once the thumb screws 336 and 338 are secured within their respective tubes 316 and 318, the filter cassette assembly 304 is fixedly secured to the manifold block 306.

A portion of the air drawn through the manifold assembly 306 is drawn through the cyclone cylinder 334, through the element 328, into the filter cassette assembly 304, through the filter 326, through the orifice element 320, through the filter passageway 310 and then through the main air passageway 308.

The sorbent tube holder 350, which may be formed, for example, from PLEXIGLASS thermoplastic material or other suitable material, is used to hold the sorbent tube 302. The tube holder 350 may preferably be used with a DELRIN thermoplastic material plug 352 with a TEFLON fluorocarban material insert 353 at its bottom and an aluminum plug 354 at its top for securing the sorbent tube 302 within the tube holder 350. An o-ring 357 may be used between the TEFLON fluorocarbon material insert 353, the passageway 355 and the sorbent tube 302. An o-ring (not shown) is also used in the aluminum plug 354 for the same purpose. Each of the DELRIN thermoplasic material and aluminum plugs 352 and 354 include threads which thread into respective threading portions on the top and bottom of the tube holder 350. A threaded nipple orifice 356 is used to connect the aluminum plug 354 to the sorbent air passageway 312. The sorbent air passageway 312 utilizes threads for that purpose, in a manner similar to the threads utilized to secure the orifice element 320 into the filter air passageway 310. Each of the aluminum and DELRIN thermoplastic material plugs 354, 352 includes an air passageway 355, or TEFLON fluorocarbon material insert 353 such that air is drawn in through the TEFLON fluorocarbon material insert 353 in the DELRIN thermoplastic material plug 352, through the sorbent tube 302, out through the air passageway 355 in the aluminum plug 354, through the nipple orifice 356 and then into the sorbent air passageway 312. Air leaving the sorbent air passageway 312 is drawn into the main air passageway 308 then ultimately to the pump 102.

The sorbent tube 302 may preferably be a Model No. 226-93 XAD-4 Sorbent Tube available from SKC, Inc. That sorbent tube, in addition to capturing nicotine, also captures 3-ethenylpyridine and myosmine. The apparatus of the present invention is also used to measure for the concentrations of those aerosol compounds in the sampled environment, in addition to nicotine. Similar sorbent tubes are available for collecting halogen containing chemicals such a chlorobenzene, carbon tetrachloride, bromoform, ethyl bromide,, chloroprene and epichlorohydrin; and other organic chemicals such as benzene, acrylonitrile, various alkanes, ethers and alcohols, aniline, napthalene, xylenes, carbon disulfide, and the like. The present invention can obviously be used to measure the concentrations of other compounds in the sampled environment, by utilizing a different sorbent tube.

Figure 4:
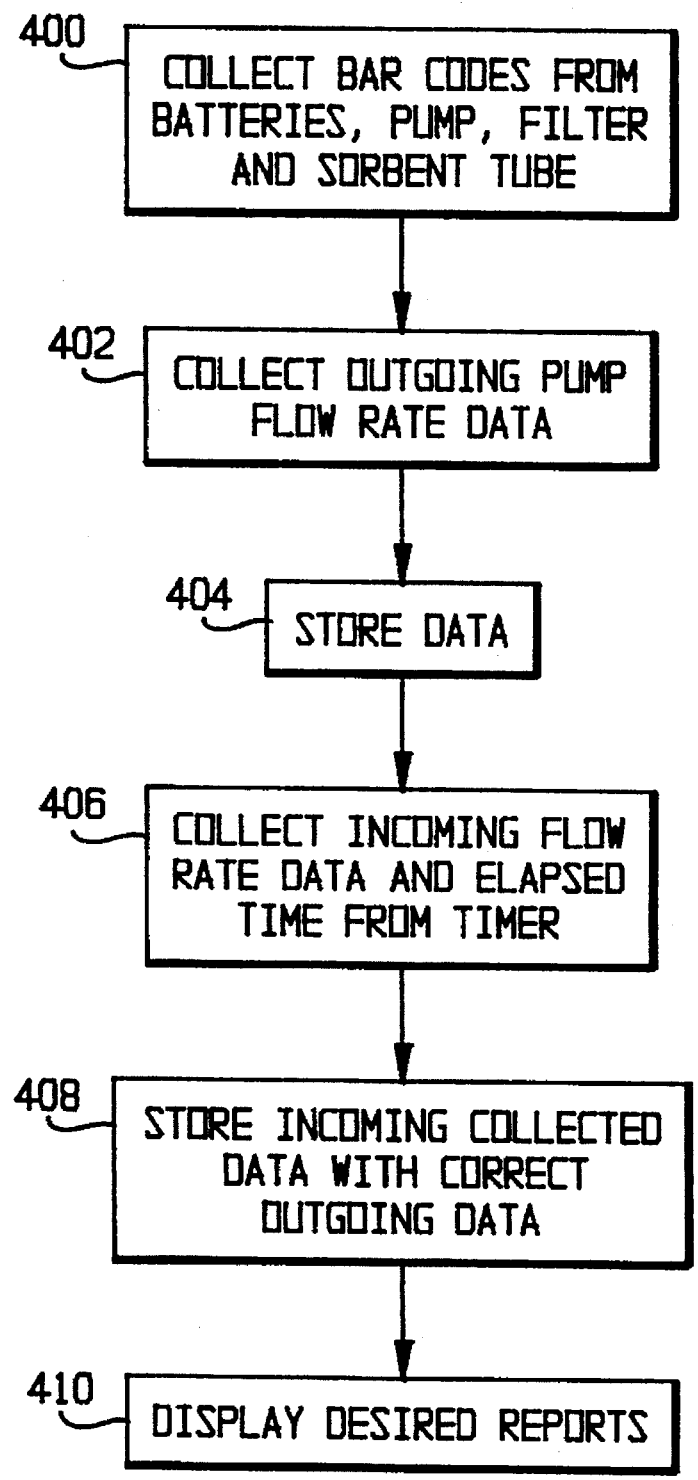
FIG. 4 is a schematic block diagram illustrating the operation of the data collection system utilized with the air sampling system of the present invention.

FIG. 4 describes the steps performed by the data logging system utilized with the microcomputer 226 described in connection with FIG. 2. The data can also be inputted manually. As shown in FIG. 4, the first step 400 is to collect the bar code information from the pump 102, the batteries 104, 106, the filter cassette 304 and the sorbent tube 302. The outgoing pump flow rate data is then collected at step 402, using the apparatus shown in FIG. 2.

The data collected in steps 400 and 402 is then stored at step 404 in a database maintained on, for example, the hard drive of the microcomputer 226. Alternatively, the data can be stored either in another form of non-volatile memory within the computer 226 or other memory of the microcomputer 226. In than manner, records of the outgoing sampling materials are created and stored in the database together with the relevant sampling information, such as outgoing flow rate data.

Once the air sampling system of the present invention has been used to collect the desired samples, it is returned to a measuring station where the sampler head 120 is again placed in the fixture 200 and connected as shown in FIG. 2. The incoming flow rate data and elapsed time data are then collected at step 406, in a manner as described in connection with steps 400 and 402. At step 408, the correct records which correspond to the incoming pump, battery, filter and sorbent identification numbers are automatically retrieved and combined with the incoming flow rate data and other data, such as time and date such information was recorded. The desired reports can then be displayed at step 410.

As will be obvious to those of ordinary skill in the art, once such data has been collected, various reports can be generated therefrom. In addition, the information contained within the database can be downloaded into ASCII files in a comma-delimited file format for easy incorporation into commonly used database and spreadsheet programs, such as EXCEL brand spreadsheet, which is available from Microsoft Corporation of Redmond, Wash. and LOTUS 1-2-3 brand spreadsheet, available from Lotus Development Corporation of Cambridge, Mass.

As will also be recognized by those of ordinary skill in the art, the elapsed time measured by the timer 108 may be inputted into the microcomputer 226 when the appropriate data screen is displayed as well as the flow rate of the pump 102, in order to calculate the concentrations of the samples obtained by the air sampling system of the present invention. While the flow rate of the pump is calibrated both before and after the sampling system is used to collect the samples, the average of the two calibrated flow rates of the pump 102 is utilized as the pump flow rate value for calculating sample concentration.

Although certain presently preferred embodiments of the invention have been described herein, it should be apparent to those skilled in the art to which the invention pertains that variations and modifications of the described embodiments may be made without departing from the spirit and scope of the invention. Accordingly, it is intended that the invention be limited only to the extent required by the appended claims and the applicable rules of law.

We claim:

1. A sampler head including a flow measuring system for use with at least two different sample collection means for use with an environmental air sampling system in which a single pump is used to draw environmental air to be sampled through said sampler head, said sampler head comprising:

a manifold block having a main air passageway fluidly connected to said pump and at least first and second parallel air passageways fluidly connected to said main air passageway;

at least two different sample collection means, each fluidly connected to one of said at least first and second air passageways such that said pump simultaneously draws air through said at least two different sample collection means; and said flow measuring system for measuring air flow through said sampler head comprises;

means for securing said sampler head in such a manner that air flow exiting from said at least two different sample collection means is separately measured while said at least two different sample collection means are in operational positions on said sampler head;

means for separately measuring said air flow exiting each of said at least two different sample collection means and for generating first signals representative of such air flow; and means for storing said first generated signals.

2. The sampler head of claim 1, wherein said one of said at least two different sample collection means collects particulate matter samples.

3. The sampler head of claim 1, wherein said one of said at least two different sample collection means collects chemical samples.

4. The sampler head of claim 2, wherein said particulate matter samples are respirable suspended particulate matter from environmental tobacco smoke.

5. The sampler head of claim 3, wherein said chemical samples are nicotine.

6. The sample head of claim 1, wherein said means for storing said first generated signals also stores later generated second signals related to air flow exiting said at least two different sample collection means after operation of said sampler head to collect air samples.

7. The sampler head of claim 1, wherein said means for storing said generated first signals also stores pump signals representative of rates of drawing environmental air through said sampler head.

8. A method for sampling environmental air in an indoor area using an air sampling system having at least two different sample collection means, each fluidly connected to one of at least first and second air passageways such that said environmental air may be simultaneously drawn through said at least two different sample collection means, comprising the steps of:

calibrating said air sampling system by measuring air flow through said air sampling system prior to its use for sampling environmental air from an indoor area;

simultaneously drawing indoor environmental air to be sampled through said at least two different sample collection means;

recording an elapsed time of said simultaneous drawing of said indoor environmental air through said at least two different sample collection means; and measuring said air flow through said air sampling system after its use for sampling environmental air from said indoor area.

9. The method of claim 8, further including the steps of:

generating at least two first data signals representative of said air flow through said air sampling system prior to its use for sampling environmental air in an indoor area;

generating at least two second data signals representative of said air flow through said air sampling system after its use for sampling environmental air from said indoor area; and storing said at least two first and second data signals and said recorded elapsed time for use in determining sample concentration in said indoor environmental air.

10. The method of claim 8, wherein said one of said at least two different sample collection means collects particulate matter samples.

11. The method of claim 8, wherein said one of said at least two different sample collection means collects chemical samples.

12. The method of claim 8, wherein said air sampling system collects indoor air samples of environmental tobacco smoke.

13. The method of claim 8, further including the step of filtering out large particulate matter contained in said environmental air drawn into said air sampling system prior to said particulate matter reaching said one of said at least two different sample collection means.

14. The method of claim 10, wherein said particulate matter samples are respirable suspended particulate matter including particulate matter from environmental tobacco smoke.

15. The method of claim 11, wherein said chemical samples are nicotine.

16. A method for sampling environmental air using an air sampling system having at least two different sample collection means, each fluidly connected to one of at least first and second air passageways such that said environmental air may be simultaneously drawn through said at least two different sample collection means, comprising the steps of:

calibrating said air sampling system by measuring air flow through said air sampling system prior to its use for sampling environmental air;

simultaneously drawing environmental air to be sampled through said at least two different sample collection means;

recording an elapsed time of said simultaneous drawing of said environmental air through said at least two different sample collection means; and measuring said air flow through said air sampling system after its use for sampling said environmental air.

17. The method of claim 16, further including the steps of:

generating at least two first data signals representative of said air flow through said air sampling system prior to its use for sampling said environmental air;

generating at least two second data signals representative of said air flow through said air sampling system after its use for sampling said environmental air; and storing said at least two first and second data signals and said recorded elapsed time for use in determining sample concentration in said environmental air.

18. The method of claim 16, wherein said one of said at least two different sample collection means collects particulate matter samples.

19. The method of claim 16, wherein said one of said at least two different sample collection means collects chemical samples.

20. The method of claim 16, further including the step of filtering out large particulate matter contained in said environmental air drawn into said air sampling system prior to said particulate matter reaching said one of said at least two different sample collection means.

* * * * *